US012685812B2

(12) United States Patent
Schlitt et al.

(10) Patent No.: US 12,685,812 B2
(45) Date of Patent: Jul. 21, 2026

(54) METHOD FOR PRODUCING A DRIP CHAMBER, DRIP CHAMBER, INFUSION SYSTEM OR TRANSFUSION SYSTEM

(71) Applicant: B. Braun Melsungen AG, Melsungen (DE)

(72) Inventors: Christof Schlitt, Frielendorf (DE); Gerrit Seidel, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 775 days.

(21) Appl. No.: 17/916,176

(22) PCT Filed: Apr. 7, 2021

(86) PCT No.: PCT/EP2021/059109
§ 371 (c)(1),
(2) Date: Sep. 30, 2022

(87) PCT Pub. No.: WO2021/204904
PCT Pub. Date: Oct. 14, 2021

(65) Prior Publication Data
US 2023/0149622 A1      May 18, 2023

(30) Foreign Application Priority Data
Apr. 9, 2020    (DE) ..................... 10 2020 204 611.5

(51) Int. Cl.
*A61M 5/14*          (2006.01)
(52) U.S. Cl.
CPC ................................ *A61M 5/1411* (2013.01)
(58) Field of Classification Search
None
See application file for complete search history.

(56) References Cited

U.S. PATENT DOCUMENTS

| 3,196,872 | A | * | 7/1965 | Katz | ..................... | A61M 39/10 |
| | | | | | | D24/129 |
| 3,967,620 | A | * | 7/1976 | Noiles | .................. | A61M 5/1411 |
| | | | | | | 604/126 |

(Continued)

FOREIGN PATENT DOCUMENTS

| CN | 106413770 A | 2/2017 |
| CN | 108697844 A | 10/2018 |

(Continued)

OTHER PUBLICATIONS

Search Report received in International Application No. PCT/EP2021/059109 dated Jul. 2, 2021, with translation, 5 pages.

(Continued)

*Primary Examiner* — Manuel A Mendez
(74) *Attorney, Agent, or Firm* — Christopher A. Rothe; CM Law

(57) ABSTRACT

A method of manufacturing a drip chamber includes connecting an upper part, a lower part, and a middle part together. The upper part and the lower part are connected in a fluid-tight manner via the middle part. Alternatively, the upper part and the lower part are directly connected in a fluid-tight manner, and the middle part is attached to the upper part and/or lower part. The middle part can create a direct fluid-tight connection with the upper part and lower part by a lower end portion of the upper part and an upper end portion of the lower part being joined to the middle part. Alternatively, the middle part bridges a lower end portion of the upper part and an upper end portion of the lower part. The lower edge of the upper part and the upper edge of the lower part are directly joined to each other.

20 Claims, 4 Drawing Sheets

(56) References Cited

U.S. PATENT DOCUMENTS

| | | | | | |
|---|---|---|---|---|---|
| 4,170,994 | A | * | 10/1979 | Komatsu | A61M 5/162 |
| | | | | | 215/47 |
| 4,395,260 | A | * | 7/1983 | Todd | A61M 5/162 |
| | | | | | 604/122 |
| 4,547,191 | A | * | 10/1985 | Ichikawa | A61M 5/14 |
| | | | | | 604/251 |
| 6,336,916 | B1 | * | 1/2002 | Bormann | A61M 5/1411 |
| | | | | | 604/407 |
| 6,800,072 | B2 | * | 10/2004 | Patzer | A61M 5/007 |
| | | | | | 222/189.09 |
| 10,485,921 | B2 | * | 11/2019 | Constuble | A61M 5/1411 |
| 2002/0029021 | A1 | * | 3/2002 | Bormann | A61M 5/1411 |
| | | | | | 604/252 |
| 2008/0140021 | A1 | | 6/2008 | Richmond | |
| 2017/0151385 | A1 | | 6/2017 | Puetter | |

FOREIGN PATENT DOCUMENTS

| | | | |
|---|---|---|---|
| DE | 2431946 | A1 | 1/1976 |
| DE | 2832504 | A1 | 2/1980 |
| DE | 19931092 | A1 | 11/2001 |
| DE | 102019205662 | A1 | 10/2020 |
| EP | 0007601 | B1 | 4/1982 |
| EP | 0355795 | A1 | 2/1990 |
| EP | 0573884 | B1 | 12/1993 |
| GB | 768689 | A | 2/1957 |
| GB | 927020 | A | 5/1963 |
| WO | 2015180892 | A1 | 12/2015 |
| WO | 2017191622 | A2 | 11/2017 |

OTHER PUBLICATIONS

Search Report received in German Application No. 10 2020 204 611.5 dated Mar. 5, 2021, with translation, 19 pages.

Written Opinion received in International Application No. PCT/EP2021/059109 dated Jul. 2, 2021, with translation, 15 pages.

Office Action received in Chinese Application No. 202180027376.X dated Sep. 22, 2023, with translation, 27 pages.

\* cited by examiner

METHOD FOR PRODUCING A DRIP CHAMBER, DRIP CHAMBER, INFUSION SYSTEM OR TRANSFUSION SYSTEM

CROSS-REFERENCE TO RELATED APPLICATIONS

This application is the United States national stage entry of International Application No. PCT/EP2021/059109, filed Apr. 7, 2021, and claims priority to German Application No. 10 2020 204 611.5, filed Apr. 9, 2020. The contents of International Application No. PCT/EP2021/059109 and German Application No. 10 2020 204 611.5 are incorporated by reference herein in their entireties.

FIELD

The present disclosure is related generally to drip chambers for infusion and transfusion systems, and more particularly to a drip chamber and method for producing a drip chamber featuring parts that are connectable to one another.

BACKGROUND

Infusions and transfusions are performed for therapeutic purposes in human and veterinary medicine. For example, infusions are used for the administration of liquid medicines (solutions of active substances, etc.). An infusion or transfusion system is understood to be a system with which the administration of a medical infusion or the performance of a medical transfusion may be carried out. In particular, it may be an infusion set (also referred to as "IV set").

An infusion or transfusion system typically comprises a tube and a drip chamber. The infusion or transfusion system may optionally include other components, such as a flow controller to control the flow rate of the fluid, such as a roller clamp. The fluid to be administered in the course of an infusion or transfusion is provided in a container. The container may be, for example, an infusion bottle, an infusion bag, a blood bag, etc.

The drip chamber is connected to the container via a container connection such that the fluid may pass from the container into the drip chamber. The container connection may, for example, comprise a piercing device, such as a hollow mandrel, which may be used to pierce a septum closing the container and which typically comprises a plurality of channels in its interior. Such a piercing device is commonly referred to as a "spike". Other systems are also known for connecting the drip chamber to the container, for example coupling systems that do not permit the drip chamber and the container to be separated once they have been connected. The drip chamber is in fluid communication with one end of the tube such that fluid may enter the tube from the drip chamber. In this sense, the drip chamber is a fluid communication system, as fluid is conducted from the container through the drip chamber into the tube. The tube comprises a connection for a patient access (e.g. venous cannula or venous catheter) at another end. The patient access may optionally also be considered part of the infusion set.

The drip chamber makes the connection between the tube and the container, as described. Usually, the devices that ensure the ventilation of the container are integrated into the drip chamber. For this purpose, the drip chamber usually comprises a venting device with a manually operated or an automatic venting valve. An air channel allows air to enter the container. To prevent contamination when air from the environment flows through the venting valve, the venting device usually comprises a venting filter. In order to ensure that liquid does not reach the venting filter and penetrate it, thus making it impermeable to air, a closing mechanism is often provided for the air channel. In the prior art, different embodiments of the venting device based on different types of valves as well as with and without a venting filter and closing mechanism are known, for example manual venting devices comprising a manually operated flap as venting valve as well as automatic venting valves comprising a check valve as venting valve. The present invention is compatible with manual and automatic venting devices.

To begin with, e.g., an infusion, i.e. to allow fluid to flow through the tube, the drip chamber is first connected to the container via the container connection. Then, the flow of the fluid must be initiated. This is usually done by squeezing the drip chamber which is made of an elastic material at least in its lower part by hand (for example between the thumb and a finger). This for example, when using a drip chamber with a spike, causes air to be pumped through one of the channels of the spike into the infusion container. The overpressure created in the infusion container initiates the flow of the liquid, i.e. the liquid starts to drip into the interior of the drip chamber. The venting valve provides the pressure equalization necessary for the fluid to continue to drip into the drip chamber by allowing air to enter through one of the channels of the piercing device (air channel), while the fluid flows out of the container into the drip chamber through another of the channels. The drip chamber returns to its original shape after force is applied to initiate the flow of the liquid. Alternatively or additionally, pressure may be applied to the container. However, since this is only possible in the case of flexible containers, most of the drip chambers available on the market comprise a flexible and thus pumpable lower section.

A drop former is provided inside the drip chamber, which causes the liquid to enter the drip chamber from the container in the form of drops of standardized size. In the case of gravity infusion, the flow rate is adjusted by the drop frequency, i.e. the number of drops per unit of time. The drop frequency is determined by the user by visually observing the drip. For some applications where an infusion pump is used to deliver the fluid, a drop sensor is used to optically measure the drop frequency. The infusion pump is controlled on the basis of the drop frequency measured in this way. For both visual observation and optical sensing, the wall of the drip chamber must be sufficiently transparent, at least in the upper section where the drop former is located.

The dimensions of a drip chamber are partly specified in the relevant standards (e.g. DIN ISO 8536-4, Part 4).

Some of the containers for infusion fluids available on the market allow the addition of further pharmaceutical products (so-called "pharmacy admixture"). The addition is carried out, for example, by injection via a port provided at the container. Usually, this port is located at a location on the container close to the position of the port through which the container connection of the drip chamber is connected to the container. The drip chamber must then be designed such that the admixture port is easily accessible to the user when the container connection of the drip chamber is connected to the container. In particular, the drip chamber must be sufficiently elongated and correspondingly narrow in shape for this purpose.

The drip chambers known in the prior art and available on the market usually comprise a short and not highly transparent upper part and a pumpable lower part. Some of the drip chambers available on the market also have a grip ring formed in the area of the outer wall of the drip chamber. The grip ring forms an elevation, which improves the manipulation of the drip chamber, as the user may securely grasp the drip chamber by the elevation with the hand. This grip ring is typically made of an opaque polymer material. It is molded onto the outer surface of the drip chamber using an injection molding process.

Depending on whether a grip ring is present or not, the term "three-part design" or "two-part design" is used.

The grip ring is conventionally formed on the outer surface of the drip chamber in a separate step. This has disadvantages, in particular there is a very high effort to provide the three-part drip chambers conventionally manufactured by the complex injection molding process. The injection molding process, which is conventionally used to form the grip ring, is very complex in terms of equipment.

Conversely, not providing the grip ring would mean losing the ergonomic advantages of the grip ring described above. In addition, the grip ring has the advantage that it hides the joint of the drip chamber such that it does not comprise any externally visible joints in the perception of the user. In addition, the material of the grip ring may be selected such that it is particularly easy to grip, which further improves manipulation. Furthermore, it is possible to give the material of the grip ring a color. By using a specific coloring, it is possible to individualize a drip chamber of a certain type or of a certain manufacturer in terms of identification. In this way, confusion in clinical use can be avoided.

In the case of the drip chambers known in the prior art and available on the market, the upper part and lower part are directly connected to each other, for example glued or welded. In addition to the high effort involved in the case of conventional drip chambers, this entails considerable restrictions in the choice of materials used for the upper part and lower part, because these materials must be selected in such a way that they can be joined to each other safely and in the simplest possible way. In other words, the materials must be compatible with each other in terms of connectivity. In addition, the materials should also meet the requirements placed on a drip chamber, for example with regard to the transparency of the upper part and the elasticity of the lower part required for pumping.

SUMMARY

Based on the above situation, it is a task of the invention to provide an improved system or manufacturing for a drip chamber for an infusion or transfusion system, an improved drip chamber for an infusion or transfusion system, and an improved infusion or transfusion system.

Due to the impossibility or difficulty of changing the complex injection molding process for forming the grip ring to the formation of a different type of grip ring made of a different material or with a different mold, it has proven to be very costly to rationally and economically form different types of drip chambers according to the modular principle because of the aforementioned requirement of material compatibility. The term "modular system" is understood to mean a concept for the design as well as for the manufacturing, in which differently designed upper parts and/or differently designed lower parts and/or differently designed middle parts are used, but each upper part, each lower part and each middle part may be used for the manufacturing of a drip chamber. In this way, drip chambers of different types can be effectively manufactured. This concerns, for example, different upper parts with different drop formers and/or different types of venting devices. This further concerns, for example, different upper parts with different qualities of transparency or optical brilliance. For example, a lower quality of transparency may be sufficient for visual observation of the drop, while a higher quality of transparency may be a prerequisite for the use of optical drop sensors. This also concerns different lower parts, such as softer ones that are easier to pump and stiffer ones that are more stable. This also concerns in general different sizes of upper and lower parts.

The method according to the invention is a method for manufacturing a drip chamber. The method herein comprises the following steps:

A) providing an upper part for the drip chamber with a first connection intended to be connected to a container, B) providing a lower part for the drip chamber with a second connection which is connected to a tube or which is intended to be connected to a tube, and C) providing a middle part for the drip chamber, D) connecting the upper part, the lower part and the middle part, such that the upper part and the lower part are connected to each other in a fluid-tight manner via the middle part, or such that the upper part and the lower part are directly connected to each other in a fluid-tight manner and the middle part is attached to the outside of the upper part and/or the lower part.

According to an embodiment of the method according to the invention, step D is carried out such that the upper part and the lower part are not directly connected to each other, but via the middle part. That is, the upper part and the lower part are not joined to each other, but are held together by the middle part. In this case, it is possible but not necessary that the upper part and the lower part touch each other in the finished manufactured drip chamber. According to this embodiment, the connection steps can be carried out in any order. It is therefore possible to connect the upper part first and then the lower part, or to join the lower part first and then the upper part to the middle part. It is also possible to connect the upper part and the lower part to the middle part at least partially at the same time. Different sequences are possible for the individual steps A, B, C and D of the method, as long as it is ensured that the parts to be connected to each other are provided in time to be connected to each other.

According to another embodiment of the method according to the invention, step D is carried out in such a way that the upper part and the lower part are directly connected to each other. The middle part is then not required to hold the upper part and the lower part together. Instead, the middle part is arranged on the outside of the hollow body consisting of the upper part and the lower part. According to this embodiment, the connection steps can be carried out in any order. It is therefore possible to connect the upper part to the middle part first and then the lower part to the upper part, or to connect the lower part to the middle part first and then the upper part to the lower part. It is also possible to first connect the upper part and the lower part to each other and then connect the middle part to the upper part, the lower part or to the upper part and the lower part. Furthermore, it is also possible to carry out all connection steps at least partially simultaneously. Different sequences are possible for the individual steps A, B, C and D of the method, as long as it is ensured that the parts to be connected to each other are provided in time to be connected to each other.

In the method according to the invention, no middle part in the form of a grip ring is molded onto the outer surface of the drip chamber by means of a complex injection molding process. Instead, a prefabricated middle part is provided. This middle part only has to be connected to the upper part and/or the lower part. This significantly reduces the manufacturing effort required to manufacture a three-part drip chamber. The reduction of the manufacturing effort is particularly useful in the present case, since infusion systems are mass-produced articles that are manufactured in large numbers.

Another advantage of the method according to the invention is that the method may very easily be converted to manufacturing a drip chamber with a different type of grip ring. For this purpose, only a different middle part has to be provided in step C. The time-consuming adaption of a production line with which the grip ring is formed by an injection molding process is not necessary.

In preferred embodiments of the method according to the invention, the connections between the individual parts are made, at least in part, by solvent bonding. This not only provides further manufacturing advantages in the sense of simplifying manufacturing, but also improves the manufactured product.

In solvent bonding, at least one of the parts to be joined to each other is treated with a suitable organic solvent. The parts to be joined are then joined to each other and preferably moved relative to each other in the form of a shear movement. According to a non-restrictive theory, the molecules of the parts to be joined become entangled with each other such that a joint is formed at the bonding site. The solvent bonding process can be implemented quickly and easily, particularly in the case of automated production. Solvent bonding is therefore a cost-effective joining method. Solvent bonding is also referred to as "solvent gluing", although it is not a gluing process in the true sense of the word, in which an adhesive glue is used to make the bonding of the joining sites.

In particularly preferred embodiments of the method according to the invention, the upper part and the lower part are not connected directly to one another, but are connected via the middle part, wherein the joining is in each case effected by solvent bonding. That is, the upper part and the lower part are not bonded to each other, but are held together by the middle part. In other words, a prefabricated middle part is used in such a way that it creates a direct fluid-tight connection with the upper part and with the lower part, respectively, for which purpose a lower end portion of the upper part and an upper end portion of the lower part are preferably bonded with the middle part, respectively.

To connect the upper part to the lower part via the middle part, on the one hand the upper part and the middle part are joined to each other by solvent bonding. On the other hand, the lower part and the middle part are joined to each other by solvent bonding. Herein, the upper part may be bonded to the middle part before the lower part is bonded to the middle part. Vice versa, the upper part may be joined to the middle part after the lower part has been joined to the middle part. Both connections can also be made at least partially simultaneously. Different sequences are thus possible for the individual steps A, B, C and D of the method, as long as it is ensured that the parts to be connected to each other are provided in time to be connected to each other. Herein, regardless of the order of the connection steps, it is possible but not necessary for the upper part and the lower part to touch each other in the finished manufactured drip chamber.

Joining the upper part to the lower part via the middle part by means of solvent bonding may, for example, allow an upper part and a lower part to be joined to each other by the advantageous technique of solvent bonding which, due to their respective materials and/or shape, could not be joined or could not be joined satisfactorily by means of solvent bonding. For example, it may be the case that the upper part is made of a first material and the lower part is made of a second material (at least in their end portions where the joint is to be made) and that no solvent is available for these materials with which solvent bonding can be performed, or only solvents which would be suitable from a chemical point of view but whose use would not be appropriate due to their evaporation properties, toxicity or other disadvantageous properties. By using a middle part consisting of a third material at least in the area of the joining sites, suitable and appropriate solvents are available for solvent bonding of the first and third or second and third materials.

Furthermore, by joining the upper part to the lower part via the middle part by means of solvent bonding, sufficiently large bonding surfaces may be provided in a simple manner, for example by using, in further preferably embodiments, an annular middle part whose bonding surfaces are arranged inside the ring. Since in this case the middle part covers the joining surfaces in the finished manufactured product, for instance the coating of the joining surfaces may result.

As an alternative to the described joining method of solvent bonding, other joining methods are in principle also possible in other embodiments depending on the nature of the materials, for example gluing using an adhesive, preferably UV gluing, in particular by means of acrylate adhesive, or welding such as mirror welding, torsion welding, and preferably ultrasonic welding. In many cases, welding methods are herein preferred because they do not require another material component.

The drip chamber according to the invention, which is obtainable in particular by the method according to the invention, comprises the upper part, the lower part and the middle part. The middle part is prefabricated according to the invention, i.e. subsequent application by injection molding is not necessary and is avoided. In a first embodiment (a), the prefabricated middle part is configured to create a direct fluid-tight connection with the upper part and with the lower part, respectively, by joining to a lower end portion of the upper part and an upper end portion of the lower part to the middle part, respectively. In this embodiment, it is sufficient that these end portions merely contact each other but are not joined to each other; the end portions may simply be adjacent to each other or are even only adjacent to each other with a gap therebetween.

In a second embodiment (b), the prefabricated middle part is configured to provide a bridging between a lower end portion of the upper part and an upper end portion of the lower part, wherein the lower edge of the upper part and the upper edge of the lower part are directly joined to each other and the middle part provides the bridging without injection molding but is optionally joined to a lower end portion of the upper part and/or to an upper end portion of the lower part. If the upper part and the lower part in this embodiment (b) are not joined to the prefabricated middle part, the middle part may simply be held in a groove formed by a smaller diameter in the transition between the lower end portion of the upper part and the upper end portion of the lower part.

Fluid-tight joining sites are guaranteed due to the prefabricated middle part, which provides a direct fluid-tight connection with the upper part and with the lower part, respectively, or which indirectly provides a bridging of upper part with lower part. Furthermore, by using a prefabricated middle part, solvent bonding or welding, in particular ultrasonic welding, at the respective joining sites with the prefabricated middle part, both fluid tightness and bridging of the seam between the upper and lower part are reliably ensured.

The drip chamber according to a particular embodiment of the invention is a drip chamber for an infusion or transfusion system, comprising an upper part with a first connection which is connected to a container or which is intended to be connected to a container, a lower part with a second connection which is connected to a tube or which is intended to be connected to a tube, and a middle part. The upper part and the lower part are each connected to the middle part in such a way that the upper part and the lower part are connected to each other in a fluid-tight manner via the middle part.

Since, according to this embodiment, the upper part and the lower part are not directly connected to each other in a fluid-tight manner but via the middle part, there is a great degree of freedom with regard to the selection of materials for the upper part and the lower part. Thus, the materials can be optimally selected with regard to the functions of the upper part and the lower part. For example, a polymer material with high brilliance may be selected for the upper part, while a polymer material is selected for the lower part that has optimal properties for pumping and is also sufficiently robust for transport and storage. Herein, the materials do not have to be matched to each other in such a way that they can be easily and safely joined directly to each other. It is only necessary to select a material for the middle part which may be joined both to both the upper part and the lower part.

Since, according to this embodiment, the upper part and the lower part are not directly connected to each other in a fluid-tight manner but via the middle part, there is a great degree of freedom with regard to the selection of joining techniques for connecting the individual parts. For example, it is possible to use a certain joining technique even if the upper part and lower part cannot be directly joined using this technique or only with great effort. It is only necessary to select a material for the middle part which may be joined to both the upper part and the lower part by means of this technique.

In particularly preferred embodiments of the drip chamber according to the invention, the upper part and the lower part are not joined directly to each other, but via the middle part, wherein the joining in each case is a joining by means of solvent bonding. That is, the upper part and the lower part are not directly joined to each other, but are held together by the middle part. In other words, the middle part creates a direct fluid-tight connection with the upper part and with the lower part respectively, for which purpose a lower end portion of the upper part and an upper end portion of the lower part are preferably joined to the middle part respectively. It is possible, but not necessary, that the upper part and the lower part touch each other in the finished manufactured drip chamber.

A connection between two parts made by solvent bonding is characterized, for example, by the fact that there is no additional material, for example in the form of an adhesive, between the parts to be joined. In addition, there are no weld beads.

Joining the upper part to the lower part via the middle part by means of solvent bonding may, for example, allow an upper part and a lower part to be joined to each other by the advantageous solvent bonding technique, which, due to their respective materials and/or shape, could not be joined or could not be joined in a satisfactory manner by means of solvent bonding.

Since the middle part, unlike the grip ring known in the prior art, does not have to be attached as a separate element in a separate manufacturing step, the manufacturing of the drip chambers according to the invention is particularly advantageous. This applies in particular because a complex injection molding process may be avoided.

According to this embodiment, the advantages of the three-part construction of the drip chamber and thus the ergonomic advantages and other advantages of a grip ring can thus be optimally realized. These include, in particular, the optimally ergonomic and intuitive manipulation, the possibility of marking different types of drip chamber or products that are different from one another in other ways, the improved possibility of modular production and therefore the simpler and more economically favorable implementation of further or other functions.

The infusion or transfusion system according to the invention is an infusion or transfusion system comprising a drip chamber according to the invention. Thus, an infusion or transfusion system is provided which has the advantageous features of the drip chamber according to the invention.

BRIEF DESCRIPTION OF THE DRAWING FIGURES

Further features, expediencies, and advantages of the invention are described below by means of exemplary embodiments with reference to the attached drawings.

DETAILED DESCRIPTION

Figure 1:
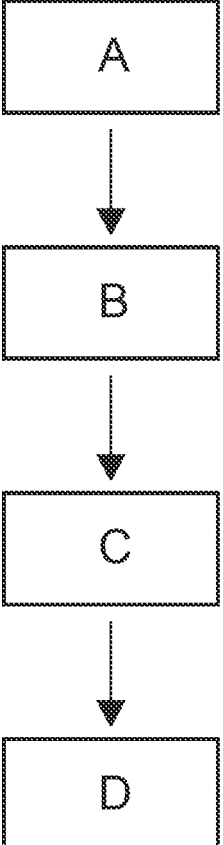
FIG. 1 shows a flowchart of an embodiment of the method according to the invention.

FIG. 1 shows a flow chart of an embodiment of the method according to the invention for manufacturing a drip chamber. The individual parts of the drip chamber are described in more detail below in the course of the description of exemplary embodiments of the drip chamber. The method according to the invention is not limited to manufacturing drip chambers according to these embodiments.

In step A, an upper part is provided. The upper part comprises a first connector which is intended to be connected to a container.

In the subsequent step B, a lower part is provided. The lower part comprises a second connection which is connected to a tube or which is intended to be connected to a tube.

In the subsequent step C, a middle part is provided. The middle part provides a grip ring in the finished manufactured drip chamber, i.e. a raised structure located on the outside of the drip chamber.

In the subsequent step D, the upper part, the lower part and the middle part are joined.

According to a first embodiment of the method according to the invention, step D is carried out in such a way that the upper part and the lower part are not directly connected to each other, but via the middle part. That is, the upper part and the lower part are not bonded to each other, but are held together by the middle part. According to this embodiment, the joining steps can be carried out in any order. It is therefore possible to join the upper part first and then the lower part to the middle part, or to join the lower part first and then the upper part to the middle part. It is also possible to join the upper part and the lower part to the middle part at least partially at the same time.

According to another embodiment of the method according to the invention, step D is carried out such that the upper part and the lower part are directly connected to each other. The middle part is then not required to hold the upper part and the lower part together. Instead, the middle part is arranged on the outside of the hollow body consisting of the upper part and the lower part. According to this embodiment, the joining steps can be carried out in any order. It is therefore possible to join the upper part to the middle part first and then the lower part to the upper part, or to join the lower part to the middle part first and then the upper part to the lower part. It is also possible to first connect the upper part and the lower part to each other and then connect the middle part to the upper part, the lower part, or to the upper part and the lower part. Furthermore, it is also possible to perform all joining steps at least partially simultaneously.

In alternative embodiments not shown in the figures, the same steps are performed in other sequences. Herein, different sequences are possible as long as it is ensured that the parts to be joined to each other are provided in time to be joined to each other.

In alternative embodiments, the middle part does not provide a grip ring in the finished manufactured drip chamber, but serves, for example, only as a connecting element that holds the upper part and lower part to each other.

In the method according to the invention, no middle part in the form of a grip ring is molded onto the outer surface of the drip chamber by means of a complex injection molding process. Instead, a prefabricated middle part is used, which only has to be connected to the upper part and/or the lower part in the course of the method, which significantly reduces the manufacturing effort required for manufacturing a three-part drip chamber. The reduction of the manufacturing effort is particularly useful in the present case, since infusion systems are mass-produced articles that are manufactured in large numbers.

In the method according to the invention, the upper part and the lower part are either each joined to the middle part or are joined directly to each other. In preferred embodiments of the invention, the joining is performed by solvent bonding.

As an alternative to the described joining method of solvent bonding, other joining methods are in principle also possible in other embodiments, depending on the nature of the materials, for example gluing using an adhesive, for example preferably UV gluing, in particular by means of acrylate adhesive, or welding such as mirror welding, torsion welding, and, preferably, ultrasonic welding. In many cases, welding processes are herein preferred because they do not require any further material component.

The joining methods mentioned (solvent bonding, welding, gluing) are associated with a lower manufacturing effort than the injection molding method conventionally used to form the grip ring. In one embodiment described, the upper part may be joined to the middle part using the same joining method as is used for joining the lower part to the middle part. However, the upper part may also be joined to the middle part by means of a different joining method than the joining used for joining the lower part to the middle part. In the other embodiment described, the middle part may be joined to the upper part and/or the lower part by means of the same joining method as the joining of the lower part to the upper part. However, the middle part may also be joined to the upper part and/or the lower part by means of a different joining method than the joining of the lower part to the upper part.

Figure 2:
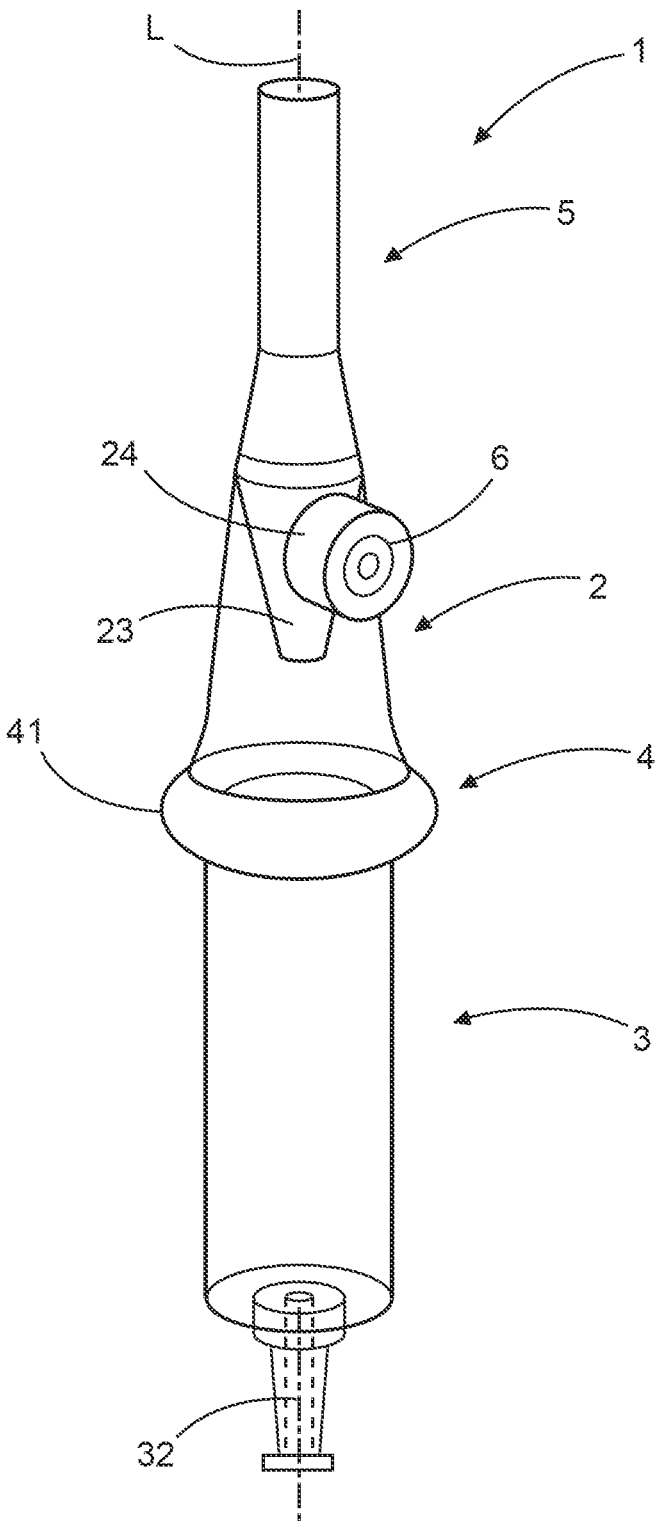
FIG. 2 shows a schematic perspective view of a drip chamber according to a first embodiment.
Figure 3:
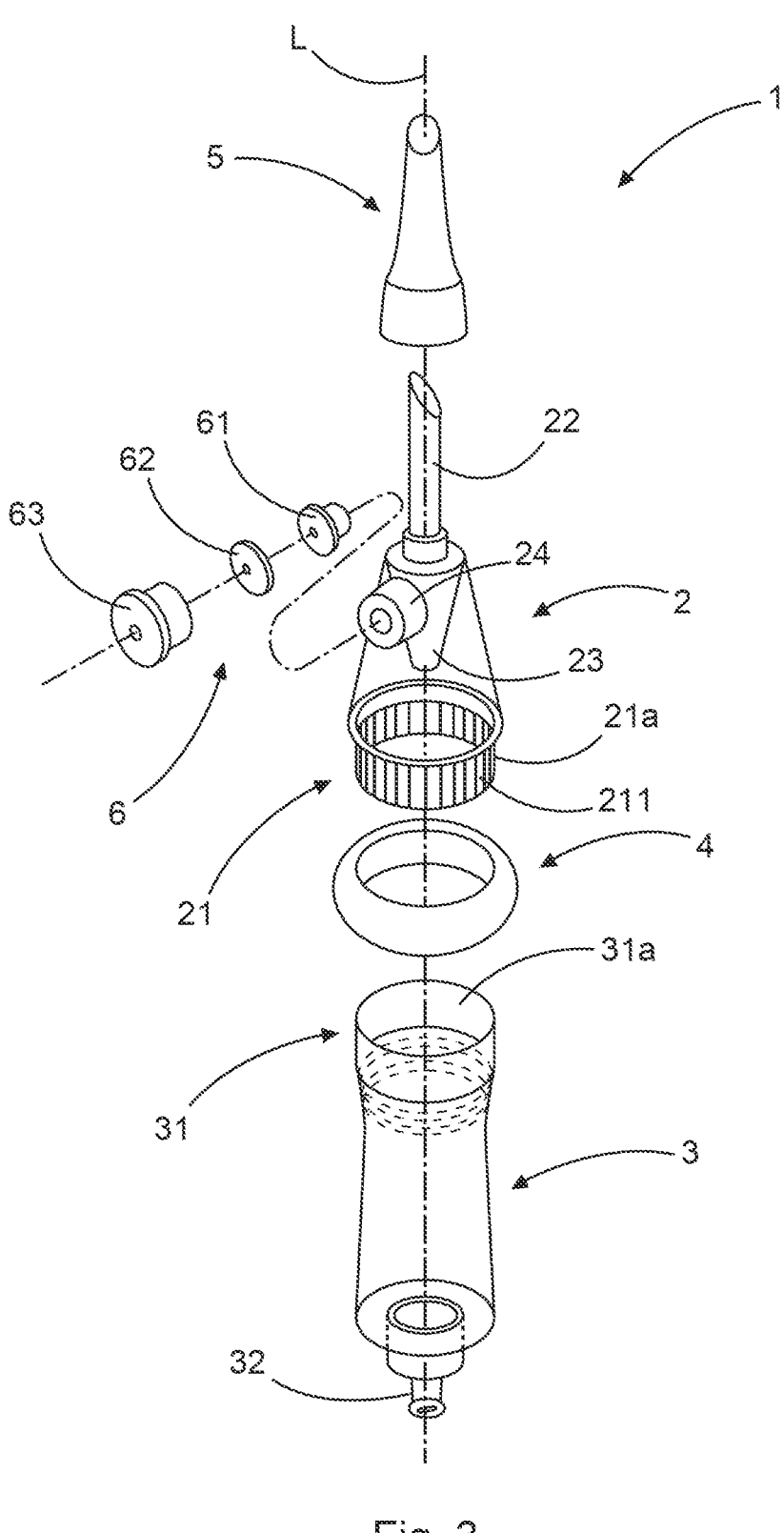
FIG. 3 shows a schematic view of the drip chamber according to the first embodiment in an exploded view.

FIG. 2 and FIG. 3 show a drip chamber 1 according to a first embodiment. The drip chamber 1 is shown in its operating position with the longitudinal axis L being vertical. In the following, the positions "upper" and "lower" ("top" and "bottom") refer to this operating position. This reference to the operating position is intended to simplify the following description. The subject-matter of the invention is not thereby limited to a particular orientation of the drip chamber 1.

The drip chamber 1 comprises an upper part 2, a lower part 3, and a middle part 4.

The upper part 2 is connected with its lower end portion 21 to the middle part 4. In the illustrated embodiment, the middle part 4 is ring-shaped. In order to improve the connection between the top part 2 and the middle part 4, joining structures 211 may be provided on the upper part 2 and/or on the central part 4. By way of example, FIG. 3 shows a corrugated structure 211 in the area of the lower end portion 21 of the upper part 2, which enables optimal joining.

The lower part 3 is connected with its upper end portion 31 to the middle part 4. In order to improve the connection between lower part 3 and middle part 4, joining structures (not shown) may be provided on bottom part 3 and middle part 4.

To improve the connection between upper part 2 or lower part 3 and middle part 4, grooves, beads or other joining structures (not shown) may be provided. Such joining structures may, for example, enable a form-fit connection and/or improve the joining surfaces for a possible connection by solvent bonding, welding, or gluing.

By having the upper part 2 and the lower part 3 each connected to the middle part 4, a fluid-tight connection is obtained between the upper part 2 and the lower part 3 via the middle part 4. That is, the drip chamber 1 forms a hollow body that is fluid-tight except for the connections and the venting device, which will be described further below.

The inner wall of this hollow body is composed of several inner wall sections, that is at least a first inner wall section corresponding at least substantially to the inner wall of the upper part 2, and a second inner wall section corresponding at least substantially to the inner wall of the lower part 3. In addition, there may be a third inner wall portion formed by a portion of the middle part 4. In other words: If the upper part 2 and the lower part 3 do not meet in abutment when they are joined to the middle part 4, the middle part 4 contributes to the formation of the wall of the drip chamber.

A first connection 22 is provided at the upper end of the upper part 2, which is opposite the lower end portion 21 of the upper part 2 in the vertical longitudinal direction L. This first port 22 is intended to be connected to a container for the liquid to be administered to the patient such that the liquid can pass from the container into the drip chamber 1, the container not being shown in the figures. In the illustration in FIG. 3, the first connection 22 is a hollow mandrel that can be used to pierce a septum that closes the container. Such a hollow mandrel having a plurality of channels in its interior is commonly referred to as a "spike". It is preferred to make the first connection 22 monolithic with the housing part of the upper part 2. The upper part 2 then consists of one piece apart from the venting device 6, which is advantageous from a manufacturing point of view and further ensures that the connection 22 is securely attached to the drip chamber 1.

In alternative embodiments not shown in the figures, other systems are provided to connect the drip chamber 1 to the container, for example coupling systems which do not allow the drip chamber and the container to be separated once they have been connected. It is also possible that the connection at the upper end of the drip chamber 1 is firmly connected to the container or the container closure, for example by solvent bonding, gluing, welding, or monolithic manufacturing methods.

A cover cap 5 may be provided to cover the first connection 22 before and optionally after use of the drip chamber 1. Covering protects the connection 22 from contamination. In addition, a sufficiently tight cover increases work safety because it protects users and patients from puncture injuries caused by a spike.

A drop former 23 is provided in the upper part 2 of the interior of the drip chamber 1. Liquid that enters the drip chamber 1 from the container through the first connection 22 enters the interior of the drip chamber 1 via the drop former 23. The drop former 23 is configured such that the liquid enters the drip chamber 1 in the form of drops of a standardized size.

The drip chamber 1 has a venting device 6. In the embodiments shown in the figures, a variant is shown in which the venting valve 61 is fitted into a venting socket 24 formed in the upper region of the upper part 2. In alternative embodiments, instead of a socket, a flat opening is provided in the wall of the upper part 2, into which the venting device is fitted.

According to the present embodiment, the venting valve 61 is a check valve which allows air to enter the container for the fluid to be administered to the patient via a channel of the connection 22, but does not allow a fluid to exit vice versa. The function of the venting valve 61 is, for example, that air is pumped into the container when the lower part 3 is compressed. This pumping function can initiate the flow of fluid from the container into the drip chamber. During pumping, the tube connected to the drip chamber is advantageously clamped, for example by means of a roller clamp customary for this purpose.

In addition to the venting valve 61, the venting device 6 comprises a venting filter 62 as well as a cap 63 which holds the venting valve 61 and the venting filter 62 around the venting socket 24.

Preferably and in contrast to the conventionally usual design, the upper part 2 has an elongated shape, i.e. its length in the longitudinal direction L is greater than its width in the direction transverse thereto. This improves the ergonomics of the drip chamber 1. In particular, the injection of medicines is facilitated because the port of the infusion container optionally provided for this purpose is more accessible to the user if the drip chamber 1 has a slender shape in the region of the upper part 2.

A second connection 32 is provided at the lower end of the lower part 3, which is opposite the upper end portion 31 of the lower part 3 in the vertical longitudinal direction L. This second port 32 is intended to be connected to a tube.

In the present embodiment example, the middle part 4 is shaped so as to provide a protrusion 41 on the outer surface of the drip chamber 1 after connection to the upper part 2 and the lower part 3. This bead 41 is, when viewed in a direction transverse to the longitudinal axis L, the widest part of the drip chamber 1. Therefore, the drip chamber 1 can be gripped particularly safely and comfortably at the bead 41, which leads to a very ergonomic and safe handling of the drip chamber 1. The protrusion thus represents a grip ring.

In a further embodiment (b) of the drip chamber according to the invention, which is not specifically shown in the figures, but which can be readily deduced from the figures, the lower edge 21*a* of the upper part and the upper edge 31*a* of the lower part are directly joined to each other, for example by solvent bonding, gluing, or welding. Herein, the middle part 4 may be joined to a lower end portion 21 of the upper part 2 and/or an upper end portion 31 of the lower part 3, but this is not required to simplify manufacture. In this case, even without being joined to upper part 2 and/or lower part 3, middle part 4 is held in the groove formed by the smaller diameter in the transition between lower end portion 21 of upper part 2 and upper end portion 31 of lower part 3.

The upper part 2 is preferably made, at least in the wall region, of an optically high-quality polymer material which is highly transparent and has a high optical brilliance. In this context, a highly transparent polymer material is understood to be a polymer material which enables at least a section of the wall of the upper part 2 to have a light transmission in the visible spectral range of at least 90%. This means that at least 90% of white light radiated onto the section of the wall of the upper part 2 passes through the section and thus less than 10% is reflected and absorbed. Preferably, the light transmission in the visible spectral range is at least 95%.

The use of a highly transparent styrene-based polymer material is preferred. The highly transparent styrene-based polymer material is, for example, polystyrene or styrene-acrylonitrile copolymer (SAN). In this way, it is possible to excellently observe the drop formation at the drop former 23 and the drop fall—either visually with the naked eye or automatically by means of an optical drop sensor. In a specific embodiment, the upper part 2, with the exception of the venting device 6, is made of highly transparent polystyrene. In an alternative embodiment, the upper part 2, with the exception of the aeration device 6, is made of highly transparent SAN.

The lower part 3 is preferably manufactured from an elastic polymer material, at least in the wall area. In this way, the pumping function of the drip chamber 1 described above may be optimally provided. Preferred is the use of a styrene-based polymer material with a suitable degree of softness matched to the desired elasticity. In particular, the use of styrene-butadiene copolymer (SBC) is preferred. In the specific embodiment described, the lower part 3 is made of SBC.

The upper part 2 and lower part 3 are each connected to the middle part 4. In preferred embodiments of the invention, the connection is provided by joining the components to each other by solvent bonding.

The material of the middle part 4 is selected such that a good connection between the components can be made in the simplest possible manner. In the specific embodiment described, the middle part 3 is made of a styrene-based polymer material which can be securely connected by solvent bonding to both the highly transparent polystyrene of the upper part 2 and the elastic polystyrene of the lower part 3. The material of the middle part 4 is thus matched to both the material of the upper part 2 and the material of the lower part 3. Preferred for the middle part is the use of a styrene-based polymeric material with a degree of softness suitable and adapted to the desired grip of the bead (grip ring). In particular, it is contemplated that the styrene-based polymer material of the middle part is also SBC.

Soft polymer materials do not generally meet the requirements placed on the upper part 2 of a drip chamber 1 in terms of translucency and optical brilliance. Highly transparent polymer materials generally do not meet the mechanical requirements placed on the lower part 3 of a drip chamber 1 in terms of pumpability. The invention allows a variety of combinations of materials for the upper part 2 and lower part 3, each of which is well suited in terms of optical or mechanical properties and fulfils the other requirements, such as chemical resistance and durability.

In further embodiments of the invention, the manipulation and safety of the drip chamber 1 is further improved in that the middle part not only provides an exposed location such as a bead or the like on the outer wall of the drip chamber 1, but is additionally made of a material that is particularly comfortable and safe to grip by hand. Soft materials and/or materials with a good grip, such as SBC, have proven to be particularly suitable for this purpose. Herein, it is not necessary that the middle part 4 as a whole is made of such a material. Rather, it is sufficient if the sections on which the drip chamber 1 is to be grasped and held are made of such a material. In specific embodiments of the invention, the middle part 4 is therefore composed of different materials, wherein at the locations where the connection to the upper part 2 and the lower part 3 is made, there is a material optimized for a particularly easy-to-manufacture and/or particularly firm connection, and at the locations where the drip chamber 1 is to be grasped and held, there is a material optimized for gripping. Herein, it is in particular possible and advantageous if the middle part 4 comprises a soft and grippy material at the locations where the drip chamber 1 is to be gripped and held, and otherwise consists of a harder material in order to provide the drip chamber 1 with additional mechanical stability.

As an alternative to the described joining method of solvent bonding, other joining methods are in principle also possible in other embodiments depending on the nature of the materials, for example gluing using an adhesive, preferably UV bonding, in particular by means of acrylate adhesive, or welding such as mirror welding, torsion welding, and preferably ultrasonic welding. In many cases, welding methods are herein preferred because they do not require another material component. Also for the alternative joining methods, the material properties of the joining components must be matched to each other such that the invention is also advantageous in connection with the alternative joining methods. In particular, it is advantageous that the mentioned joining methods are associated with a lower manufacturing effort than the injection molding method conventionally used for forming the grip ring. The upper part 2 may be joined to the middle part 4 using the same joining method as method for joining the lower part 3 to the middle part 4. The upper part 2 may also be joined to the middle part 4 using a different joining method than the method for joining the lower part 3 to the middle part 4.

Figure 4:
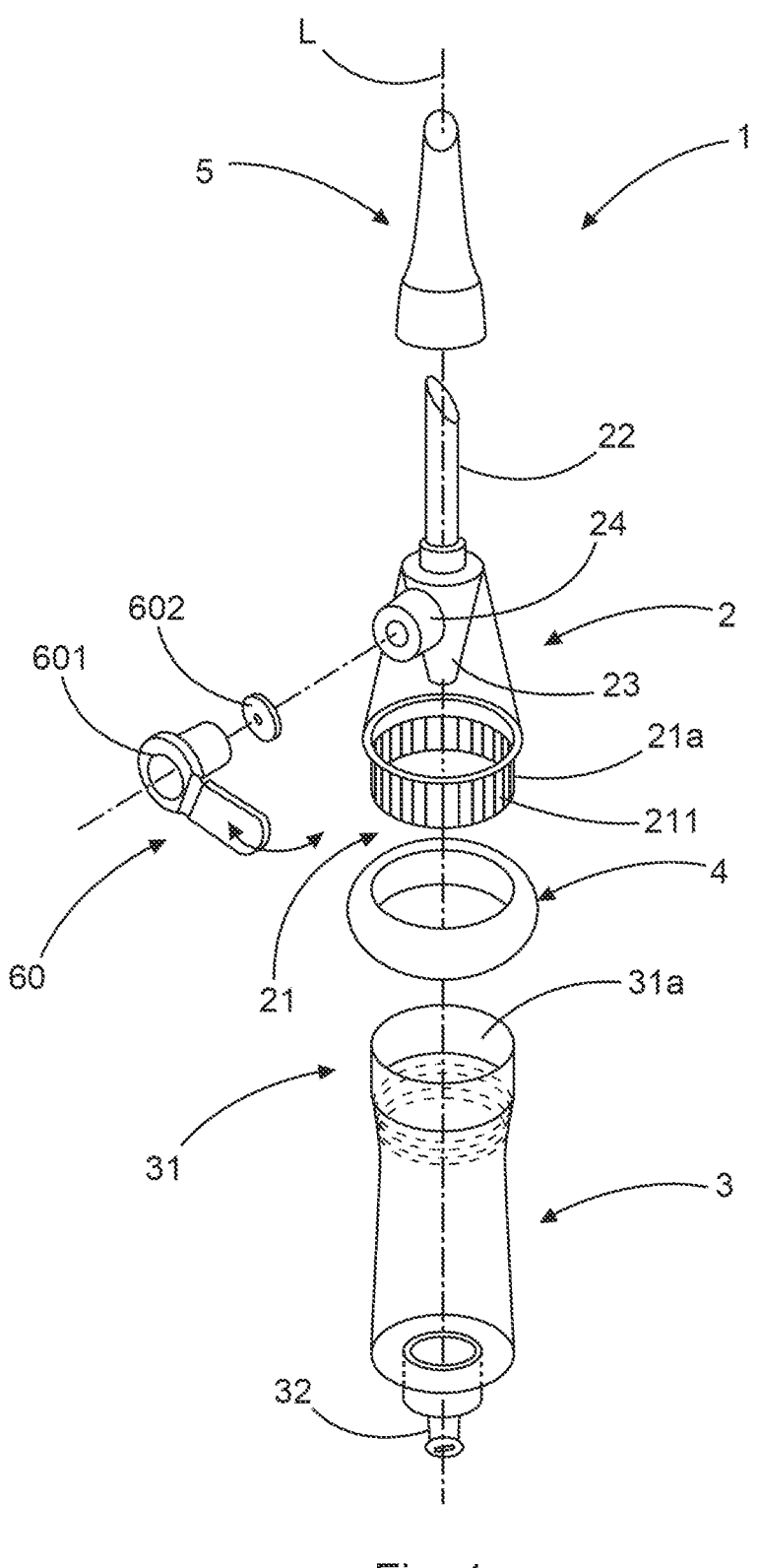
FIG. 4 shows a schematic view of the drip chamber according to a second embodiment in an exploded view.

FIG. 4 shows a schematic view of the drip chamber 11 according to a second embodiment in an exploded view. The drip chamber 11 according to the second embodiment differs from the drip chamber 1 according to the first embodiment only with respect to the venting device. The other elements correspond to each other and are marked with the same reference signs. A more detailed description of the other elements and their function is therefore redundant.

The venting device 60 of the drip chamber 11 according to the second embodiment comprises, in addition to the venting valve 601, a venting filter 602.

The venting valve 601 is a flap which may be opened and closed manually. The function of the venting device 60

(second embodiment) corresponds to the function of the venting device 6 (first embodiment) described above.

The outer shape of the upper part is conical in the embodiments shown above. In alternative embodiments not shown in the figures, the upper part may also comprise another basic shape, it may for example be cylindrical or dome-shaped.

The outer shape of the lower part is cylindrical in the embodiments shown above. In alternative embodiments not shown in the figures, the lower part may also comprise another, for example conical, basic shape.

In the embodiments shown above, apart from the venting device, the drip chamber comprises rotational symmetry with respect to a rotation about the longitudinal axis L. In alternative embodiments not shown in the figures, the drip chamber may also be non-rotationally symmetrical, for example comprising elliptical cross-sections.

The middle part 4 of the drip chamber 1 according to the invention may be formed as a sleeve, which ensures the fluid-tight connection of the upper part 2 and the lower part 3. In this case, it is possible that the upper part 2 and the lower part 3 are each connected to the middle part 4 in such a way that the upper part 2 or its lower edge 21a and the lower part 3 or its upper edge 31a are spaced apart from one another and there is, for example, a circumferential gap between the upper part 2 and the lower part 3. In this case, the middle part 4, via which the upper part 2 and the lower part 3 are connected to each other, contributes to forming the inner wall of the drip chamber 1. However, the upper part 2 and the lower part 3 can also be arranged in such a way that the lower edge 21a of the upper part 2 and the upper edge 31a of the lower part 3 are in abutment, i.e. the upper part 2 and the lower part 3 are then not spaced apart but touch each other. The middle part 4 then has the function of holding the upper part 2 and the lower part 3 in this position relative to each other and, if necessary, further sealing the connection between upper part 2 and lower part 3. In this case, the middle part 4 does not contribute to forming the inner wall of the drip chamber 1.

In summary, an embodiment of the invention may be described as follows: A method of manufacturing a drip chamber 1, comprising the steps of providing an upper part 2, a lower part 3 and a middle part 4 and connecting the upper part 2, the lower part 3 and the middle part 4. The connecting is performed such that the upper part 2 and the lower part 3 are connected to each other in a fluid-tight manner via the middle part 4, or such that the upper part 2 and the lower part 3 are directly connected to each other in a fluid-tight manner and the middle part 4 is attached to the outside of the upper part 2 and/or the lower part 3.

According to the invention, a drip chamber 1 is thus obtained which comprises, for example, in addition to the upper part 2 and the lower part 3, a prefabricated middle part 4 which is configured to provide a direct fluid-tight connection with the upper part and with the lower part, respectively, by joining a lower end portion 21 of the upper part 2 and an upper end portion 31 of the lower part 3 to the middle part 4, respectively, or which is configured to provide bridging of a lower end portion 21 of the upper part 2 and an upper end portion 31 of the lower part 3, wherein the lower edge 21a of the upper part and the upper edge 31a of the lower part are directly joined to each other and the middle part 4 provides the bridging.

The invention claimed is:

1. A method of manufacturing a drip chamber comprising the steps of:

A) providing an upper part for the drip chamber with a first connection connectable to a container;

B) providing a lower part for the drip chamber with a second connection connectable to a tube;

C) providing a middle part for the drip chamber, the middle part being formed and provided separately from the upper part and the lower part;

D) placing the upper part into direct contact with the lower part to form a continuous chamber therebetween;

E) positioning the middle part to surround both the upper part and the lower part;

F) bonding the upper part to the middle part to form a first fluid-tight connection; and G) bonding the lower part to the middle part to form a second fluid tight connection, wherein the upper part is not bonded directly to the lower part in the completed drip chamber.

2. A drip chamber manufactured by the method according to claim 1.

3. A drip chamber for an infusion or transfusion system, the drip chamber comprising:

an upper part having a first connection connectable to a container;

a lower part with a second connection connectable to a tube; and a middle part that is prefabricated separately from the upper part and the lower part, wherein a lower end portion of the upper part and an upper end portion of the lower part are directly contacting and not directly bonded to each other, and the middle part is joined to a lower end portion of the upper part at a first fluid tight connection and to an upper end portion of the lower part at a second fluid tight connection.

4. The drip chamber according to claim 3, wherein:

the first fluid tight connection comprises a first solvent bond or weld, and the second fluid tight connection comprises a second solvent bond or weld.

5. The drip chamber according to claim 4, wherein:

the upper part comprises a first polymer material, the lower part comprises a second polymer material that is different from the first polymer material, the middle part comprises a third polymer material that is different from the first polymer material and the second polymer material, and the first polymer material is not bondable with the second polymer material by solvent bonding or welding, the first polymer material is bondable with the third polymer material by solvent bonding or welding, and the second polymer material is bondable with the third polymer material by bonding or welding.

6. The drip chamber according to claim 5, wherein the first polymer material, the second polymer material and/or the third polymer material is a styrene-based polymer material.

7. The drip chamber according to claim 6, wherein the first polymer material a polystyrene material or a styrene-acrylonitrile copolymer material.

8. The drip chamber according to claim 7, wherein the polystyrene material is a highly transparent polystyrene material, or wherein the styrene-acrylonitrile copolymer material is a highly transparent styrene-acrylonitrile copolymer material.

9. The drip chamber according to claim 6, wherein the third polymer material is a styrene-butadiene copolymer material.

10. The drip chamber according to claim 6, wherein the third polymer material is a styrene-butadiene copolymer material.

11. The drip chamber according to claim 3, wherein at least a portion of a wall of the upper part has a light transmission in a visible spectral range of at least 90%.

12. The drip chamber according to claim 3, wherein the middle part provides a protrusion on an outer surface of the drip chamber.

13. The drip chamber according to claim 3, wherein the first connection is formed as a piercing device for piercing a wall or a septum of a container for a liquid to be administered to a patient, and/or wherein the first connection is connected to the container in a non-detachable manner.

14. The drip chamber according to claim 3, wherein the second connection comprises a coupling device connectable to a complementary coupling device at an end of a tube such that a tight fluid connection exists between an interior of the drip chamber and the tube.

15. An infusion or transfusion system comprising a drip chamber according to claim 3.

16. The drip chamber according to claim 3, wherein the middle part surrounds an outer surface of the upper part and an outer surface of the lower part.

17. The drip chamber according to claim 16, wherein the upper end portion of the lower part surrounds the lower end portion of the upper part.

18. The drip chamber according to claim 16, wherein a lower end portion of the upper part comprises a corrugated structure.

19. The drip chamber according to claim 18, wherein the corrugated structure comprises a cylindrical body having corrugations extending along an axis extending from the first connection to the second connection.

20. A drip chamber for an infusion or transfusion system comprising:

an upper part with a first connection connectable to a container;

a lower part with a second connection connectable to a tube; and a middle part, wherein the upper part and the lower part are each connected to the middle part with the middle part surrounding an outer surface of the upper part and an outer surface of the lower part, such that the upper part and the lower part are each connected to the middle part in a fluid-tight manner, and the upper part and the lower part are not connected directly to each other.

* * * * *